United States Patent

Hendricks et al.

[11] 3,989,772
[45] Nov. 2, 1976

[54] N,N-BIS-(PHOSPHONOMETHYL)-ACRYLAMIDES

[75] Inventors: Udo Winfried Hendricks, Cologne; Klaus Walz, Bergisch-Neukirchen, both of Germany

[73] Assignee: Bayer Aktiengesellschaft, Leverkusen-Bayerwerk, Germany

[22] Filed: Oct. 9, 1974

[21] Appl. No.: 513,487

[30] Foreign Application Priority Data

Oct. 12, 1973  Germany............................ 2351295

[52] U.S. Cl............................ 260/932; 260/502.5; 260/927 R; 260/969
[51] Int. Cl.² ............................................ C07F 9/40
[58] Field of Search ................................... 260/932

[56] References Cited
UNITED STATES PATENTS 3,711,577  1/1973  Maier................................... 260/932
3,823,206  7/1974  Golborn et al....................... 260/932

Primary Examiner—Anton H. Sutto
Attorney, Agent, or Firm—Plumley and Tyner

[57] ABSTRACT

N,N-bis-(phosphonomethyl)-acrylamides of the formula

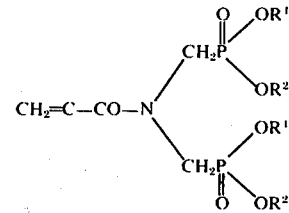

in which
R represents hydrogen, methyl or ethyl and
$R^1$ and $R^2$ represent $C_1$-$C_4$-alkyl, which is optionally substituted by halogen, or hydrogen, alkali metal, half an equivalent of an alkaline earth metal or ammonium, or together with the oxygen atoms and the phosphorus atom from a five-membered to seven-membered heterocyclic structure

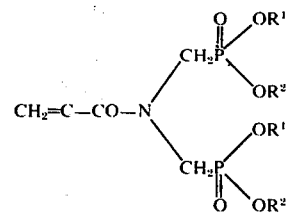

and a process for their preparation.

1 Claim, No Drawings

N,N-BIS-(PHOSPHONOMETHYL)-ACRYLAMIDES

The invention relates to new N,N-bis-(phosphonomethyl)-acrylamides of the formula

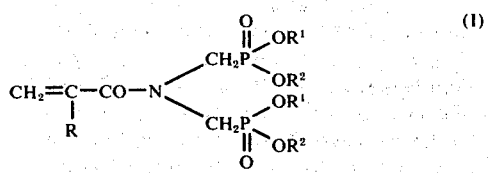

in which
R represents hydrogen or the methyl or ethyl radical and
$R^1$ and $R^2$ inndependently of one another represent a $C_1-C_4$-alkyl radical which is optionally substituted by halogen atoms, preferably chlorine or bromine atoms, or represent hydrogen or an alkali metal, half an equivalent of an alkaline earth metal or ammonium ion, or together with the oxygen atoms and the phosphorus atom form a five-membered to seven-membered heterocyclic structure
and to a process for their preparation.

The compounds of the formula I are prepared by a method wherein bis-(halogenomethyl)-acrylamides of the formula

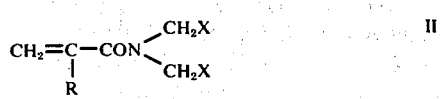

in which
R has the abovementioned meaning and
X represents a chlorine or bromine atom are reacted with phosphorous acid trialkyl esters of the formula

in which
$R^3$, $R^4$ and $R^5$ independently of one another represent a $C_1-C_4$-alkyl radical which is optionally substituted by halogen atoms, preferably chlorine or bromine atoms, or
$R^3$ and $R^4$ together with the oxygen atoms and the phosphorus atom form a five-membered to seven-membered heterocyclic structure,
optionally in diluents which are inert under the reaction conditions, at temperatures of 40°–160° C, preferably 60°–120° C.

The following may be mentioned as examples of representatives of the phosphorous acid trialkyl esters of the formula III: trimethyl phosphite, triethyl phosphite, dimethylethyl phosphite, tri-isopropyl phosphite, tri-n-propyl phosphite, dimethyl-n-propyl phosphite, tri-n-butyl phosphite, tri-isobutyl phosphite, tris-(2-chloroethyl) phosphite, tris-(2-bromoethyl) phosphite, 2-methoxy-1,3-dioxaphospholane and 2-ethoxy-4-methyl-1,3-dioxa-phospholane.

The following may be mentioned as examples of bis-halogenomethyl-acrylamides of the formula II: acrylic acid N,N-bis-(chloromethyl)-amide, acrylic acid N,N-bis-(bromomethyl)-amide, methacrylic acid N,N-bis-(chloromethyl)-amide, methacrylic acid N,N-bis-(bromomethyl)-amide and ethacrylic acid N,N-bis-(chloromethyl)-amide.

The compounds of the formula II are prepared by reacting acrylamides of the formula

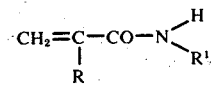

in which
R has the abovementioned meaning and
$R^1$ represents hydrogen, a hydroxymethyl group or a lower alkoxymethyl group
with formaldehyde or compounds which give off formaldehyde and organic or inorganic acid halides.

In the reaction according to the invention of the compounds of the formula II with the phosphorous acid trialkyl esters of the formula III it is desirable continuously to remove the compounds $R^5$-X produced in the reaction, for example methyl chloride, ethyl chloride or ethylene chloride, from the reaction mixture, for example by distillation or by introducing a stream of inert gas.

In general, the compounds of the formulae II and III are employed in the molar ratio of 1:2, but it is also possible to use the phosphorous acid trialkyl esters III in a slight excess.

Examples of possible diluents which are inert under the reaction conditions are hydrocarbons, such as toluene, xylene and n-nonane, or dimethylformamide.

Preferred compounds of the formula I are prepared by reaction of N,N-bis-(chloromethyl)-acrylic acid amide and methacrylic acid amide with trimethyl phosphite, triethyl phosphite or tris-(2-chloroethyl) phosphite.

The compounds of the formula I in which
$R^1$ and/or $R^2$ represent hydrogen or an alkali metal, alkaline earth metal or ammonium ion
are obtained in a known manner by the dealkylation or hydrolysis of the phosphonic acid ester; on this subject see, for example, Houben-Weyl "Methoden der organischen Chemie" ("Methods of Organic Chemistry"), 4th edition 1963, volume 12/1, pages 410–412.

The new compounds of the formula I are colourless, stable liquids which can usually not be distilled without decomposition. They are capable of diverse use. Thus, for example, new compounds with valuable properties can be obtained by addition of compounds with active hydrogen atoms to the double bond of the compounds of the formula I. For example, the addition reaction with long-chain amines gives surface-active compounds from which compounds having a bactericidal action can be obtained by alkylation or saponification.

The compounds can furthermore be polymerised, or be reacted with other polymerisable monomers to give copolymers, in the customary manner. Furthermore, the compounds of the formula I are suitable for use as flameproofing agents for textiles of natural and/or synthetic fibres, and for plastics, paper and other materials.

EXAMPLE 1

400 parts of N,N-bis-(chloromethyl)-methacrylamide are added slowly to 620 parts of trimethyl phosphite at 80°–90° C. The methyl chloride produced is collected in a cold trap. After completion of the addition, the mixture is heated to 110°–120° C for 1 hour. The volatile constituents are then distilled off, initially at 10–20 mm Hg and then at 1 mm Hg. 650 parts of the compound

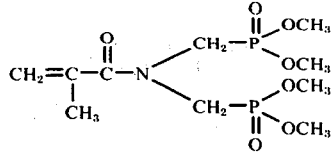

are obtained as a colourless liquid which cannot be distilled without decomposition.

$C_{10}H_{21}NO_7P_2$ (molecular weight 329) $n_D^{20} = 1.4788$. Calculated: C, 35.5%; H, 6.38%; N, 4.26%; P, 18.85%. Found: C, 35.7%; H, 6.4%; N, 4.4%; P, 18.4%.

EXAMPLE 2

91 parts of N,N-bis-chloromethyl-methacrylamide are added slowly to 166 parts of triethyl phosphite at 125° C. The resulting ethyl chloride is collected in a cold trap. After completion of the addition, the mixture is stirred for a further 15 minutes at 130°–140° C. Volatile constituents are distilled off at 90°–100° C under a vacuum down to 0.5 mm Hg. 186 parts of the compound

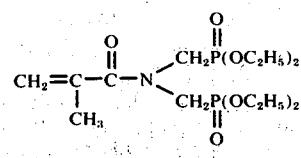

are obtained as a pale yellow-coloured liquid which cannot be distilled without decomposition.

$C_{14}H_{29}NO_7P_2$ (molecular weight 385) $n_D^{20} = 1.4971$. Calculated: C, 43.6%; H, 7.54%; N, 3.64%; P, 16.1%. Found: C, 43.6%; H, 7.5%; N, 3.8%; P, 15.8%.

EXAMPLE 3

270 parts of tris-(2-chloroethyl) phosphite and 91 parts of N,N-bis-(chloromethyl)-methacrylamide are simultaneously introduced dropwise, from separate dropping funnels, into a flask heated to 100°–110° C. The ethylene chloride produced is distilled off during the reaction at 25 mm Hg. After completion of the addition, the mixture is stirred for a further half hour at 100°–120° C and the volatile constituents are then distilled off under a vacuum down to 1 mm Hg. 270 parts of the compound

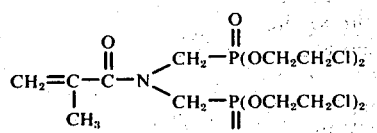

are obtained as a colourless liquid which cannot be distilled.

$C_{14}H_{25}Cl_4NO_7P_2$ (molecular weight 523) $n_D^{20} = 1.4972$. Calculated: C, 32.1%; H, 4.78%; N, 2.68%; Cl, 27.2%; P, 11.85%. Found: C, 31.7%; H, 4.8%; N, 2.6%; Cl, 27.5%; P, 11.5%.

EXAMPLE 4

N,N-bis-(Chloromethyl)-methacrylamide can be prepared as follows:

172 parts of N-methoxymethyl-methacrylamide are mixed with 0.67 part of powdered potassium hydroxide and 0.67 part of hydroquinone and 48 parts of paraformaldehyde are added in portions at 70° C. The mixture is heated to 110° C and is stirred for one-half hour at this temperature. The resulting reaction mixture is now added dropwise over the course of 3 hours, at 40° C, to a solution of 357 parts of thionyl chloride in 200 parts by volume of methylene chloride. A further 5 parts of paraformaldehyde are then added and the mixture is stirred for a further 2 hours at 40° C. After cooling to room temperature, the reaction solution is freed from small amounts of a precipitate by filtration and is concentrated in vacuo down to 1.5 mm Hg and at a temperature of 40° C. The residue is distilled on a film evaporator at 145° C and 2–3 mm Hg. 117 parts of the compound

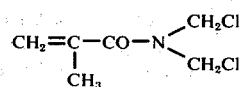

are obtained as a colourless liquid.

$C_6H_9Cl_2NO$ (molecular weight = 182) $n_D^{20} = 1.4989$. Calculated: C, 39.5%; H, 4.95%; Cl, 39.0%; N, 7.7%. Found: C, 38.8%; H, 4.8%; Cl, 38.5%; N, 7.7%.

EXAMPLE 5

850 parts of methacrylic acid amide, 800 parts of dioxane, 2,020 parts of triethylamine and 20 parts of pulverulent potassium hydroxide are mixed and at 70° – 80° C 660 parts of paraformaldehyde are added. The mixture is stirred for one-half hour, cooled and added dropwise to a solution of 2380 parts of thionyl chloride in 2000 parts by volume of tetrachloride methane at a temperature of 40° – 50° C over the course of 24 hours. The mixture is stirred for a further 3 hours at 50° – 55° C, a further 8 hours at 70° C, cooled and filtered off by suction from the precipitated salt. The filtrate is then concentrated in vacuo and distilled off on a film evaporator at 120° – 130° C and 1 – 3 mm Hg. 420 parts of the product described in Example 4 are obtained.

We claim:

1. N,N-bis-(Phosphonomethyl)-acrylamides of the formula

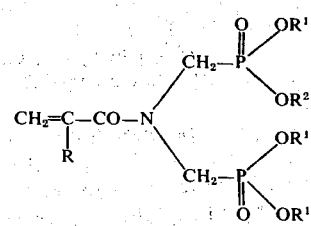

in which
R represents hydrogen or the methyl or ethyl radical and
$R^1$ and $R^2$ independently of one another represent methyl, ethyl or chloroethyl.

* * * * *